United States Patent [19]

Heinsohn et al.

[11] Patent Number: 5,726,123
[45] Date of Patent: Mar. 10, 1998

[54] METHOD FOR TREATING COTYLEDONOUS PLANTS

[75] Inventors: George E. Heinsohn, Elkton, Md.; August S. Bjornson, Wilmington, Del.

[73] Assignee: DCV Chitin Technologies, L.P., Wilmington, Del.

[21] Appl. No.: 799,741

[22] Filed: Feb. 12, 1997

[51] Int. Cl.⁶ .............................. A01N 43/16; C05F 1/00; C08B 37/08

[52] U.S. Cl. .................. 504/140; 504/100; 504/118; 504/147; 504/292; 504/319; 504/326; 504/335; 71/16; 71/27; 536/20; 514/55

[58] Field of Search .................................. 504/100, 118, 504/140, 147, 292, 319, 326, 335; 71/16, 27; 536/20; 514/55

[56] References Cited

U.S. PATENT DOCUMENTS

| | | | |
|---|---|---|---|
| 3,922,260 | 11/1975 | Peniston et al. | 536/20 |
| 4,812,159 | 3/1989 | Freepons | 504/147 |
| 4,886,541 | 12/1989 | Hadwiger | 504/100 |
| 4,964,894 | 10/1990 | Freepons | 504/292 |
| 4,978,381 | 12/1990 | Hadwiger | 504/292 |
| 5,104,437 | 4/1992 | Hadwiger | 514/55 |
| 5,554,445 | 9/1996 | Struszczyk | 428/403 |

FOREIGN PATENT DOCUMENTS 195 03 465 A1   2/1995   Germany.

*Primary Examiner*—John Pak

[57] ABSTRACT

Application of an aqueous solution containing a chitosan salt and oligomers of chitosan to the foliage of growing plants increases the yield of vegetables, tubers, cereal grains, fruits, and blossoms.

13 Claims, No Drawings

METHOD FOR TREATING COTYLEDONOUS PLANTS

FIELD OF INVENTION

The invention is directed to a method for treating cotyledonous plants to improve the yield, health, and vigor of the plant by spraying an aqueous solution containing chitosan oligomers and a chitosan salt onto the leaves of the plant.

BACKGROUND OF THE INVENTION

Chitosan is a naturally occurring polymer found in many fungi. It may be broadly described as a copolymer of D-glucosamine and N-acetyl-D-glucosamine in which 65–100 % of the monomer units are D-glucosamine. Since it is a member of the chemical class known as amines, which are weakly basic, it readily and reversibly forms salts with acids such as mineral acids and carboxylic acids. Many of these salts are water soluble. In a system in which chitosan and an acid are present, both (1) electrically neutral glucosamine units and (2) units in which the glucosamine unit is protonated and associated with the anion corresponding to the acid will be present in the polymer chain in proportions which are dependent on pH. Such a system is commonly referred to as a chitosan salt without regard to the extent to which the glucosamine units are protonated. For clarity and brevity, such systems will hereinafter be referred to as chitosan salts but it is to be understood that such terminology includes species in which free amino groups may be present.

It has been amply demonstrated that application of chitosan salts to the seeds of cereal crops results in dramatic changes in the biochemistry of the emergent plant. Included among these changes are an increased production of a class of compounds known as the phytoalexins, which provide protection against localized microbial infection, and increased production of callose and lignin, which provide structural strength and a barrier to the spread of infection. These changes occur as a result of activation of the gene encoding the enzyme phenylalanine ammonia lyase, which is involved in the rate determining step of the phenylpropanoid metabolism pathway.

Chitosan has been shown to induce synthesis of the terpenoid phytoalexins which are closely involved in the biosynthesis of growth hormones such as gibberelic acid and abscisic acid. Chitosan induces activation of genes which produce chitinase and glucanase enzymes that are known to be both fungal inhibitors and to play a role in pollen development and seed germination. Chitosan also induces activation of genes which produce protease inhibitors that help protect the plant from insect attack. On a macroscopic scale, these changes translate into enhanced root development, reduced lodging (plants falling over before harvest), enhanced yield, and resistance to certain plant diseases.

U.S. Pat. No. 4,812,159 (Freepons) discloses in detail treatment of soil in a seed planting zone with a solution of chitosan, application of a chitosan solution to plant seeds, treatment of soil in the seed planting zone with a mixture of solid chitosan and a solid acid, and treatment of soil in the seed planting zone with a solid chitosan salt. The preferred chitosan solution was one that contains more than 1.5 equivalents of glutamic acid per mole of amino function in the chitosan. Application of chitosan to the foliage of an emerging plant is mentioned, but there is no disclosure of the methods required to accomplish such treatment, nor of the results thereby achieved. For all of these treatments by Freeports, it is stipulated that when an acidic component is used in making the chitosan preparation, the acid must be selected from the group of non-phytotoxic acids, which are defined as those that will not cause a significant adverse effect on germination of seeds or on the developing seedling. U.S. Pat. No. 4,964,894 is a continuation-in-part of U.S. Pat. No. 4,812,159 and notes that glutamic acid, tartaric acid, citric acid, adipic acid, hydrochloric acid, formic acid, and nitric acid meet the criteria of non-phytotoxicity. Acetic acid and butyric acid were found to be phytotoxic and harmful to the development of the plant seedling. This would make these acids unsuitable for use according to the Freepons' teaching.

Treatment of seed is accomplished according to the teachings of U.S. Pat. No. 4,812,159 by applying a chitosan preparation to seed or by immersing the seed in such a preparation, followed by drying. The drying is necessary to prevent premature germination of the seed in the time interval between treatment and planting. In the absence of a drying step, it is recommended that planting occur within 60 hours of seed treatment. While seed treatment is easily accomplished on a small scale using the methods disclosed, the treatment protocols cannot be extended to commercial scale operations without invention of specialized equipment or modification of equipment commonly used in the seed coating industry such as grain augering devices like the Gustavson seed coater. This is a serious drawback in commercial seed-coating operations where the same piece of equipment must also be used to apply other treatments (e.g., fungicides) to seeds and cannot be dedicated for use only with chitosan. Furthermore, the treatment is limited to a single application of chitosan at the very earliest stage of plant growth which is not repeated and reinforced at other key stages of plant growth such as flowering, seed formation, and ripening.

Treatment of soil in the seed planting zone with a chitosan preparation requires the preparation to be distributed in a region in close proximity to where the seed will be planted. Specialized equipment is therefore required to target the treatment to the region where the seed will eventually germinate. While this may be readily accomplished in the case of mechanized seeding, this technique is not compatible with other methods such as aerial seeding or broadcast seeding. In addition, the two techniques utilizing chitosan in the form of a solid require that the solid be introduced in the form of very small particles (0.5–100 μm) which therefore require elaborate pre-processing of the chitosan to put it in a form suitable for application. As with seed treatment, treatment of soil in the region of seed germination is limited to a single treatment at the very earliest stage of plant growth lest the root system of the plant be disrupted.

Since no method is disclosed for application of chitosan to the foliage of the emerging plants, it is not known if this technique provides any beneficial effect. Clearly though, it shares with the other methods the limitation that treatment is constrained to the earliest stage of plant growth.

U.S. Pat. No. 4,964,894 describes again the same techniques noted above and then goes on to describe a procedure for identifying non-phytotoxic acids. Glutamic acid, tartaric acid, citric acid, adipic acid, hydrochloric acid, formic acid, and nitric acid were found to meet the criteria for non-phytotoxicity. Acetic acid and butyric acid were found to be phytotoxic and therefore detrimental to development of the seedling. The preferred chitosan solution is one that contains more than 1.5 equivalents of glutamic acid per mole of amino function in the chitosan.

Another technique is described in U.S. Pat. No. 5,554,445 (Kivekas, Struszczyk) which involves spraying seeds with a liquid dispersion of microcrystalline chitosan followed by drying to form a polymer film around the seed. In order to form an appropriate film on the seed, it is specified that the chitosan must have a water retention value of 200–5,000 %, hydrogen bonding potential of 10–25 kJ/mol, and particle size of 0.1–100 μm. As noted above, these procedures require specialized equipment, elaborate pre-processing of the chitosan, and are limited to a single treatment at the earliest stage of plant growth.

U.S. Pat. No. 4,886,541 (Hadwiger) discloses the application of a chitosan preparation to wheat seed in order to enhance yield, reduce lodging, and enhance root development. The treatment is accomplished by applying an aqueous solution of chitosan acetate to the seed in a manner such that the seed is agitated to disburse the liquid on the seed. Recommended techniques are the use of a grain augering device or cement mixing equipment. As discussed above, application of chitosan to seeds by the teachings of this disclosure adds complexity and cost to commercial seed coating, and is limited to a single application at the earliest stage of plant growth. U.S. Pat. No. 4,978,381 (Hadwiger) and U.S. Pat. No. 5,104,437 (Hadwiger) describe the same techniques for seed treatment and provide additional examples to extend the method to other cereal crops such as flee, oats, barley, and rye.

Applicants' co-pending U.S. patent application Ser. No. 08/787,870, filed on Jan. 23, 1997, discloses a method for treating plants by foliar application of a chitosan salt solution that results in increased yield, better drought resistance, and improved overall vigor. The chitosan salt is prepared from chitosan of molecular weight greater than 50,000 amu (atomic mass units, daltons) and an acid that forms a water-soluble chitosan salt in proportions such that the ratio of acid equivalents to amino groups is 1.02–1.20.

Chitosan has been employed in agriculture for purposes other than its ability to enhance crop yields. It has also demonstrated properties as a bactericide against a variety of microorganisms and has been used where this property may be put to good advantage. The use of chitosan to inhibit frost damage is disclosed in JP 07179843 A (assigned to Daiiche Seimo KK), wherein spinach leaves inoculated with the ice-nucleating organisms *Pseudomonas syring* and *Pantoea agglomerants* were treated with chitosan and then exposed to freezing temperature. The treated leaves had significantly less frost damage than the controls.

In addition, U.S. Pat. No. 5,374,627 discloses the use of a chitosan hydrolysate of molecular weight 10,000–50,000 prepared by high-temperature, acid-catalyzed degradation of chitosan as an effective agent for protecting plants against a number of plant diseases such as bacterial soft rot (vegetables), spring deadspot (turfgrass), and bacterial grain rot (rice).

SUMMARY OF THE INVENTION

The invention is therefore directed to the application of a solution containing both a chitosan salt and chitosan oligomers to the foliage of growing plants to enhance the yields of vegetables, seeds, fruits, tubers, and blossoms. Plants so treated are healthier, more drought resistant, and many plant varieties enjoy an extended production period. The treatment may be repeated throughout the growth cycle of the plant, especially during critical stages of plant growth such as flowering, seed formation, and ripening.

The invention is therefore directed primarily to a method for improving the yield, health, and vigor of growing cotyledonous plants comprising (1) spraying onto the foliage between appearance of the first true leaves and harvest of the plant or fruit therefrom an aqueous solution containing dissolved therein 0.01–1.50% by weight of a water-soluble salt of chitosan and an acid, in which solution the ratio of acid equivalents to amino groups derived from the chitosan is 1.02–1.20, and also dissolved therein 0.1–15.0% chitosan oligomers based on the weight of the chitosan salt (exclusive of anion) and (2) repeating step (1) before harvesting the plant or useful portion thereof.

In a further aspect, the invention is directed to the above-described treating solution. In a still further aspect, the invention is directed to a method for preparing the above described treating solution comprising (1) dispersing particles of chitosan in water at 45–85C and adding thereto an acid that forms a water-soluble salt when reacted with chitosan, in an amount such that the ratio of acid equivalents to amino groups derived from the chitosan is 1.01–1.20, and (2) adding thereto chitosan oligomers in an amount such that the oligomers are equal to 0.1–15.0% of the chitosan weight (exclusive of anion).

DEFINITION

As used herein, the term "harvest" and various forms thereof refer not only to gathering the useful or edible portion of growing plants, but also to gathering the entire plant. Examples of the former are picking fruit from trees, picking beans from vines, picking ears of corn from the stalks, cutting cabbage and celery, etc. Examples of the latter are the digging of root vegetables such as potatoes, beets, and carrots.

DETAILED DESCRIPTION OF THE INVENTION

A. Composition of Chitosan

Though chitosan is a naturally occurring polymer found in many fungi, it is neither abundant nor readily isolated from natural sources in high purity. As a matter of convenience, chitosan is more readily obtained from chitin which, after cellulose, is the second most abundant natural polymer. Chitin is readily isolated from shellfish or insect exoskeletons and is also found in mollusks and fungi. It is a water insoluble copolymer of N-acetyl-D-glucosamine and D-glucosamine, but the great preponderance of monomer units consist of N-acetyl-D-glucosamine residues. Chitosan is a copolymer of the same two monomer units, but the preponderance of monomer units are D-glucosamine residues. Since the D-glucosamine residues bear a basic amino function, they readily form salts with acids. Many of these salts are water soluble. Treatment of chitin with concentrated caustic at elevated temperature converts N-acetyl-D-glucosamine residues into D-glucosamine residues and thereby converts chitin into chitosan. A convenient method of obtaining chitosan from the chitin found in shellfish waste is described in U.S. Pat. No. 3,862,122 (Peniston). Although there is a continuum of compositions possible between pure poly-N-acetyl-D-glucosamine and pure poly-D-glucosamine, the term chitosan is generally applied to those polymers containing 65–100 % of D-glucosamine residues. Compositions within this range are soluble in acidic solutions; but if more than about 35% of the monomer residues are N-acetyl-D-glucosamine, the polymer is insoluble in weakly acidic solutions.

Commercially available chitosan is typically prepared from shellfish and has a molecular weight measured in the hundreds of thousands, corresponding to polymer chains in which several thousand monomer units are linked together in β-1,4 fashion. Chitosan obtained from fungal sources is typically of somewhat lower molecular weight and may contain fractions with molecular weight as low as 50,000 amu (atomic mass units, daltons). For present purposes the term chitosan is intended to apply to copolymers of D-glucosamine and N-acetyl-D-glucosamine containing 0–35% N-Acetyl-D-glucosamine residues and having a molecular weight greater than 50,000 amu and corresponding to polymer chains in which about 250 or more monomer units are joined together (degree of polymerization or DP=250). The chitosan used in this study was obtained from shrimp or crab shell and contained about 75–82% D-glucosamine residues, which is typical of commercially produced chitosan. It was readily soluble in dilute aqueous solutions of both mineral and carboxylic acids.

B. Composition of Chitosan Oligomers

Techniques are well known in the literature for causing scission of chitosan chains using acid or enzyme catalysts. Depending on the starting material and reaction conditions chosen, the extent to which chain scission occurs can be controlled so that the resulting fragments are large enough still to be considered as chitosan (DP>250). At the other extreme, chain scission can be conducted under conditions so rigorous that the only products are the monomeric species D-glucosamine and N-acetyl-D-glucosamine (DP=1). For present purposes, the term "chitosan oligomers" is intended to refer to those copolymers of D-glucosamine and N-acetyl-D-glucosamine having a degree of polymerization (DP) of 2 to 50 corresponding to a molecular weight of about 320 to 10,000 amu. Procedures for preparing such chitosan oligomers by acid catalysis have been described by Horowitz, Roseman, and Blumenthal (*J. Amer. Chem. Soc.*, 1957, 79, 5046–49). Procedures for preparing such chitosan oligomers by enzymatic cleavage have been described by Li, Brzezinski, and Beaulieu (*Plant Physiol. Biochem.*, 1995, 33 (5), 599–603. The chitosan oligomers used in the present study were prepared by a modification of the methods of Li, et.al.

A mixture of chitosan oligomers and chitosan salt may be applied to the foliage of growing plants by spraying with a solution containing appropriate amounts of these materials, or by other techniques which will be readily apparent to one skilled in the art. The preferred technique is by solution spraying which eliminates the problems associated with settling of dispersions, or the dust inhalation hazard associated with applying solids to the plant. It is preferred to use solutions having a chitosan salt concentration (exclusive of anion) of 0.01% to 1.5% and most preferred to use solutions with concentration of 0.05 to 0.50%. Solutions in this concentration range have viscosities compatible with commercial spraying equipment. Furthermore, they require an application rate of 5–50 gallons per application per acre to achieve correct dosage, which is compatible with the normal operation of commercial spraying equipment. It is preferred to use solutions in which the chitosan oligomers are present in amounts equal to 0.05–50% and preferably 0.1–15%, based on the weight of chitosan salt therein (exclusive of anion).

C. Acids

Many of the acids which form water soluble chitosan salts are themselves detrimental to growing plants, making it important to prevent exposure of the plants to high concentrations of these acids. On the other hand, unless a large excess of acid (measured as equivalents of acid per mole of amino function in the chitosan) is employed to prepare the chitosan salt solution, chitosan dissolves only very slowly in acidic solution at ambient temperature. One technique for solving this dilemma is to select only those more expensive acids which are least phytotoxic such as glutamic acid so that a large excess of acid can be used to form the solution while limiting damage to the plant. A second technique is to employ a large excess of acid during the dissolution step and then neutralize the excess with base after dissolution is complete. This procedure is unsatisfactory since great care is required to prevent localized pH excursions in the region where base is introduced. Such an excursion converts the chitosan salt back into electrically neutral chitosan which precipitates from solution. The precipiate is then very slow to redissolve since there is no longer a large excess of acid present. Therefore, the preferred technique is to use only a very small excess of an inexpensive acid and to perform the dissolving step at elevated temperature. By limiting the excess of acid employed, the phytotoxic effect of the acid can be reduced to undetectable levels. Satisfactory rates of dissolution can be achieved even with only a slight excess of acid by performing the_dissolution at elevated temperature. It is most preferred to use acetic acid which is inexpensive and is readily available at a ratio of 1.02–1.20 moles acetic acid per mole of amino groups in the chitosan. This is in sharp contrast to the teachings of U.S. Pat. No. 4,812,159 and U.S. Pat. No. 4,964,894 which found acetic acid to be phytotoxic and therefore unsuitable for forming chitosan solutions to be used for applications described therein. It is preferred to perform the dissolving step at 50–75C. In this fashion, chitosan can be dissolved at a 2.5% concentration in 3–5 hr. This concentration is suitable for efficient transport to the application site and is of sufficiently low viscosity that on-site dilution with water is straightforward.

Suitable acids for making the chitosan salts for use in the invention are those which form water-soluble salts with chitosan. It is not necessary that the acid itself be water-soluble; however such water-soluble acids are preferred because of ease in handling them. Inorganic acids which form water-soluble chitosan salts include the halogen acids and nitric acid. Sulfuric and phosphoric acids are excluded because they do not form water-soluble salts with chitosan. Organic acids are preferred and include the following: lactic acid, glycolic acid, glutamic acid, and acetic acid. Either mono- or poly-functional carboxylic acids can be used, which can be aliphatic or aromatic, so long as they form water-soluble salts with chitosan.

D. Additives

As used herein, the term "additives" refers to materials which may be optionally used to augment the effectiveness of the invention, but do not themselves have bio-activity. These include such materials as surfactants, wetting agents, defoaming agents, extenders, penetrants, activators, spreading agents, diluents, odorants, brightening agents and the like. It is particularly preferred to use a small amount of wetting agent in the compositions in order to obtain even distribution and wetting of the hydrophobic surface of the plant leaves. Such agents are usually used in concentrations of 0.01–0.1% by weight.

E. Coadjuvants

As used herein, the term "coadjuvant" refers to materials that have a bio-activity that may be the same or different than the bio-activity of the chitosan salts. Such materials include fertilizers, fungicides, insect repellents, trace nutrients, pesticides, herbicides, and mixtures thereof. Both liquid and solid coadjuvants can be used in conjunction with water-soluble chitosan salts and oligomers, so long as the resultant aqueous compositions are sprayable.

F. Method for Making Chitosan Oligomer/Chitosan Salt Solution

A preferred method for making the treating solution is to form an aqueous dispersion of chitosan at a temperature of 45–85C (preferably at 55–75C) and then to add the acid. Under these reaction conditions the particle size of the chitosan is not critical. It is preferred that the reaction temperature be at least 45C in order to have a rapid rate of reaction without the necessity of using a large excess of acid. On the other hand, it is preferred that the reaction temperature not exceed 85C in order to avoid discoloration and to assure stability of the water-soluble salt. Chitosan oligomers, additives, and coadjuvants can be added to the reaction solution at any stage. Nevertheless, in order to minimize any secondary reactions, it is preferred that they be added after the reaction is complete and the solution has cooled.

G. Method for making Chitosan Oligomers

Chitosan oligomers were prepared by adding chitosanase enzyme (from the actinomycete Kitasatosporia N174) to a solution of chitosan acetate at 37–55C. After 31 hr, the mixture was heated to 85C to denature the enzyme. The product was concentrated under vacuum at 35–40C and then lyophilized to dryness. Size exclusion chromatography on a Supelco-TSK Column G-Oligo-PW with a mobile phase containing 0.03 M acetic acid and 0.2 M sodium sulfate revealed that 41% of the resolved oligomers were of DP (degree of polymerization) <7 and 59% of DP 6–28.

H. Method of Application

One clear advantage of the invention is that the chitosan oligomer/chitosan salt solution can be applied to the plants by liquid spraying, which is the most economical and efficient method of application for both large and small agricultural areas. The aqueous compositions can be applied by other liquid application methods such as brushing. However, they are less efficient.

As mentioned above, compositions of the invention are applied to the first true leaves of the growing plant and preferably at least twice again before harvesting of the plant, preferably at flowering and at the onset of maturation.

It is not necessary to evaporate the applied solution. In fact, it is preferred not to do so for the reason that adsorption of the chitosan salt and chitosan oligomers into the plant takes place from the liquid state. However, evaporation of the solution to dryness will ordinarily take place due to normal atmospheric conditions of temperature and humidity.

I. Safety

A further advantage of the invention is that the chitosan compositions are non-toxic. For example, chitosan glutamate has an acute oral LD50 of more than 5g/kg in rats (5 male, 5 female albino rats). Furthermore, the compositions have an acute dermal $LD_{50}$ greater than 2g/kg on rabbits (5 male, 5 female albino rabbits). Because of such low toxicity, the compositions of the invention are not toxic to birds, mammals, or humans. Moreover, the low toxicity level and easy biodegradability of the compositions act to prevent detrimental effects on the beneficial constituents of fertile soil layers. Accordingly, EPA has established an exemption from the requirement of a tolerance for residues of poly-D-glucosamine, when they are used in the production of raw agricultural commodities.

J. Test Procedures

The following procedures were employed in the below-described examples.

A chitosan acetate solution was prepared by vigorously stirring an appropriate amount of water at a temperature of 60° C. and adding small flakes of chitosan containing 80% D-Glucosamine residues at such a rate that the chitosan became wetted and dispersed throughout the liquid phase. Glacial acetic acid was then added in the ratio of 0.36 lb. of acetic acid per pound of chitosan. This represents a ratio of 1.03 equivalents of acetic acid per mole of amino function in the chitosan. The mixture was stirred at 60C until substantially all the chitosan had dissolved. The resulting solution then filtered through coarse cheese cloth to remove any adventitious particles. The quantities of water and chitosan were chosen so that the chitosan concentration (exclusive of the acetate anion) was 5.0%. Solid chitosan oligomers were added equivalent to 10% of the weight of chitosan (exclusive of anion) and the mixture briefly agitated to ensure dissolution of the oligomers. This solution was then further diluted with water to a chitosan salt concentration of 2.5% wt. and packaged in units containing 304 g. for transport to the trial site. On-site dilution of the package provided the correct amount of chitosan oligomer/chitosan salt solution to fill a 2 gallon garden sprayer with a solution containing 0.1% chitosan salt and 0.01% chitosan oligomers.

For crops that were planted as seed or tubers (squash, corn, bean, potato), treatment was commenced as soon as the plant had produced its first set of true leaves. The true leaves are those which follow the emergent leaves (cotyledons) and resemble the leaves of the mature plant in shape. For crops that were obtained as established greenhouse seedlings (tomatoes), treatment was commenced at the time of transplanting outdoors. In either case, the treatment was repeated at intervals of two to three weeks throughout the growing season. The treatment protocol was to spray the foliage of the plant until the top of the leaf surfaces were thoroughly wetted and solution began to drip from the leaf tips. To the extent possible, this treatment was performed just after irrigation so that there was no substantial difference in moisture available to the treated plants compared to the controls. As the plants increased in size, it was obviously necessary to use more chitosan oligomer/chitosan salt solution to wet the leaves. It was estimated that the treatment rate was 5–10 gallons/acre for the initial treatment and 20–40 gallons/acre at end of treatment. For crops that are optimally harvested before the mature stage such as squash, the number of fruits rather than total weight was used as a measure of enhanced production. For crops that are harvested at maturity such as beans and corn, total crop weight was used as a measure of enhanced production.

K. Treatable Plants

A wide variety of cotyledonous plants can be advantageously treated by the method of the invention, so long as the treatment is carded out in the manner described above. Such plants include members of the genera Allium, Appium, Asparagus, Beta, Brassica, Capsicum, Citrullis, Cucurbita, Daucus, Frageria, Lactuca, Lycopersicum, Phasedus, Solanum, Spinachia and Zea. Among the members of these genera of vegetables are asparagus, beans, beets, broccoli, carrots, celery, corn, egg plant, lettuce, melons, onions, pea, peppers, potatoes, spinach, squash, strawberries and tomatoes.

EXAMPLES

Example 1

Hills of squash (Burpee Yellow Summer) each containing 3 plants were planted side-by-side in late May, 1996 in soil that had been prepared simply by turning and breaking up clods. Cultivation and irrigation were applied to all hills in identical fashion as required during growth. One hill was treated with chitosan oligomer/chitosan salt solution by the procedure described above and the other served as control. Fruits were harvested as they reached preferred size between July 9 and August 8. The study was terminated on August 8 due to an infestation of borers. The treated plants afforded 40 fruits compared to 28 fruits for the control. This represents a yield enhancement of 43%.

Example 2

Parallel rows of green beans were planted in identical fashion in late May, 1996 in soil that had been prepared by mining, breaking up clods, and raking smooth. Both rows were cultivated and irrigated as required during growth. One row was treated with chitosan oligomer/chitosan salt solution as described above while the other served as control. The crop was harvested at weekly intervals until Aug. 26 when it was judged that the plants were spent. The treated row produced 13 lb 6 oz of beans compared to 11 lb 6 oz for the control. This represents a yield enhancement of 18%.

Example 3

Seedling tomatoes (Brandywine) were transplanted outdoors on Jun. 2, 1996, into soil that had been prepared by cultivating and raking smooth. One half the plants were treated with chitosan oligomer/chitosan salt solution as described above while the other half served as control. Both groups were cultivated, irrigated, and supported in equivalent fashion as required throughout the growing season, and fruits harvested as they ripened. A total of 86 fruits were harvested from the treated group of plants compared to 74 fruits from the control group. This represents a yield enhancement of 16%.

Example 4

Two ninety foot rows of sweet corn (Seneca Star) were planted in soil that had been tilled and smoothed. One row was treated with chitosan oligomer/chitosan salt solution as described above while the other served as control. The rows were grown under identical conditions and harvested during the period Jul. 20-Jul. 29, 1996. The treated row yielded 57.25 lb (111 ears) of product and the control yielded 43.50 lb (110 ears) of product. This represents a yield enhancement of 32%.

Example 5

One hundred hills of red potatoes were divided into a test group and control group of 50 hills each and grown under identical conditions except that the test group was treated with chitosan oligomer/chitosan salt solution as described above. Tubers were periodically examined and harvested as soon as they reached target size. It was judged that this occurred by Aug. 5, 1996, for the test group and the test plants were accordingly harvested yielding 97.50 lb of potatoes (average weight=0.15 lb). The control group was harvested on Aug. 14, 1996, yielding 82.15 lb of potatoes (average weight=0.127 lb). This represents a yield increase of 19%, achieved in 9 fewer growing days.

What is claimed is:

1. A method for improving the yield of growing cotyledonous plants having their first true leaves comprising (1) applying to the exposed surface of the leaves an aqueous liquid solution having dissolved therein (a) 0.01–1.5% by weight of a salt of chitosan prepared by reaction of chitosan with an acid, in which solution the ratio of acid equivalents to amino groups derived from the chitosan is 1.02–1.20, and (b) 0.05–50% of chitosan oligomers selected from the group consisting of copolymers of D-glucosamine and N-acetyl-D-glucosamine having a degree of polymerization of 2 to 50, based on the weight of chitosan salt exclusive of anion, and (2) repeating step (1) at least one time before harvesting the plant.

2. A composition for treating cotyledonous plants having their first true leaves comprising an aqueous solution containing (a) 0.01–1.5% by weight of a salt of chitosan prepared by reaction of chitosan with an acid, in which solution the ratio of acid equivalents to amino groups derived from the chitosan is 1.02–1.20, and (b) 0.05–50% of chitosan oligomers selected from the group consisting of copolymers of D-glucosamine and N-acetyl-D-glucosamine having a degree of polymerization of 2 to 50, based on the weight of chitosan salt exclusive of anion.

3. The method of claim 1 in which the acid equivalents are derived from a carboxylic acid.

4. The method of claim 3 in which the carboxylic acid is selected from the group consisting of acetic, glutamic, lactic and glycolic acids and mixtures thereof.

5. The method of claim 1 in which at least a portion of the plant is edible by humans.

6. The method of claim 5 in which the plant is an edible vegetable.

7. The method of claim 6 in which the plant genus is selected from the group consisting of Allium, Atrium, Asparagus, Beta, Brassica, Capsicum, Citrullis, Cucurbita, Daucus, Frageria, Lactuca, Lycopersicum, Phasedus, Solanum, Spinachia and Zea.

8. The method of claim 7 in which the plant is selected from the group consisting of asparagus, beans, beets, broccoli, carrots, celery, corn, egg plant, lettuce, melons, onions, peas, peppers, potatoes, spinach, squash, strawberries and tomatoes.

9. The method of claim 8 in which the plant is beans.

10. The method of claim 8 in which the plant is corn.

11. The method of claim 8 in which the plant is squash.

12. The method of claim 8 in which the plant is potato.

13. The method of claim 8 in which the plant is tomato.

* * * * *